US011534561B2

(12) United States Patent
Kasuya et al.

(10) Patent No.: US 11,534,561 B2
(45) Date of Patent: Dec. 27, 2022

(54) INSUFFLATION DEVICE AND METHOD OF ADJUSTING INTRA-ABDOMINAL PRESSURE

(71) Applicant: OLYMPUS CORPORATION, Tokyo (JP)

(72) Inventors: Yuma Kasuya, Hachioji (JP); Takefumi Uesugi, Tachikawa (JP); Koji Yamaoka, Hamura (JP); Kunitoshi Hiraga, Tama (JP); Shinya Torii, Tokyo (JP); Keita Kimura, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 17/026,953

(22) Filed: Sep. 21, 2020

(65) Prior Publication Data

US 2021/0001059 A1      Jan. 7, 2021

Related U.S. Application Data

(63) Continuation of application No. PCT/JP2018/028911, filed on Aug. 1, 2018.

(30) Foreign Application Priority Data

Mar. 26, 2018   (JP) .............................. JP2018-058797

(51) Int. Cl.
    *A61M 13/00*    (2006.01)
(52) U.S. Cl.
    CPC ... *A61M 13/003* (2013.01); *A61M 2205/3334* (2013.01); *A61M 2205/3344* (2013.01); *A61M 2205/3355* (2013.01); *A61M 2205/50* (2013.01)

(58) Field of Classification Search
    CPC ........ A61M 13/003; A61M 2205/3334; A61M 2205/3344; A61M 2205/50;
    (Continued)

(56) References Cited

U.S. PATENT DOCUMENTS 6,402,714 B1    6/2002   Kraft-Kivikoski

FOREIGN PATENT DOCUMENTS

JP    5-269079 A    10/1993
JP    5-329164 A    12/1993
(Continued)

OTHER PUBLICATIONS

International Search Report dated Oct. 23, 2018 received in PCT/JP2018/028911.

*Primary Examiner* — Amber R Stiles
*Assistant Examiner* — Avery Smale
(74) *Attorney, Agent, or Firm* — Scully, Scott, Murphy & Presser, P.C.

(57) ABSTRACT

An insufflation device includes: a gas feeding conduit for feeding a predetermined gas which is fed from a gas supply source into a body cavity; and a processor. The processor measures a gas feeding time period until a predetermined amount of the gas is fed according to a set pressure, measures a pressure in the body cavity, calculates a gas discharging time period based on the set pressure and a measurement result of the measured pressure; and adjusts a gas feeding flow rate of the gas according to a difference between the measured gas feeding time period and the calculated gas discharging time period.

19 Claims, 7 Drawing Sheets

(58) Field of Classification Search
CPC .......... A61M 2205/3355; A61M 13/00; A61M 13/006; A61M 5/168; A61M 5/16804; A61M 5/16877; A61M 5/16881; A61M 5/16886; A61M 5/172; A61M 2202/0225; A61M 2205/3331; A61M 2205/3337; A61M 2205/3341
See application file for complete search history.

(56) References Cited

FOREIGN PATENT DOCUMENTS

| | | | |
|---|---|---|---|
| JP | H05329164 A | * | 12/1993 |
| JP | 9-75355 A | | 3/1997 |
| JP | H0975355 A | * | 3/1997 |

\* cited by examiner

INSUFFLATION DEVICE AND METHOD OF ADJUSTING INTRA-ABDOMINAL PRESSURE

CROSS REFERENCE TO RELATED APPLICATION

This application is a continuation application of PCT/JP2018/028911 filed on Aug. 1, 2018 and claims benefit of Japanese Application No. 2018-058797 filed in Japan on Mar. 26, 2018, the entire contents of which are incorporated herein by this reference.

BACKGROUND OF THE INVENTION

1. Field of the Invention

The present invention relates to an insufflation device and a method of adjusting an intra-abdominal pressure.

2. Description of the Related Art

Recently, for a purpose of alleviating invasiveness to a patient, laparoscopic surgery where therapeutic treatment is performed without laparotomy has been performed. In the laparoscopic surgery, for example, a first trocar which introduces an endoscope for observation into a body cavity and a second trocar which introduces a treatment instrument into a part to be treated are punctured into an abdominal part of a patient. In the laparoscopic surgery, using an endoscope which is inserted into an abdominal cavity through an insertion hole for the first trocar, treatment or the like is performed by observing the part to be treated and the treatment instrument inserted through an insertion hole for the second trocar.

In laparoscopic surgery, an insufflation device is used for ensuring a field of view of the endoscope and for ensuring a region for operating the treatment instrument. The insufflation device expands a body cavity by setting a pressure in a body cavity to a constant pressure by injecting, for example, a carbon dioxide gas as an insufflation gas into the body cavity thus ensuring a field of view of the endoscope and an operation region for the treatment instrument.

In general, the insufflation device also performs measurement of a pressure in the body cavity using a gas feeding tube which is used for feeding a gas into the body cavity. Accordingly, after feeding of a gas into the body cavity is performed for a predetermined time period, feeding of the gas is temporarily stopped, and a pressure in the body cavity is measured. Such intermittent gas feeding is performed until the pressure in the body cavity reaches a set pressure.

In the laparoscopic surgery, gas discharging is also performed for discharging a smoke or a mist generated due to the use of the treatment instrument or the like to the outside of the body. Accordingly, the insufflation device also has a gas discharging mode which makes use of suction equipment which a facility such as a hospital has.

For example, Japanese Patent Application Laid-Open Publication No. 5-329164 discloses an insufflation device having such a gas discharging mode.

For example, when a user presses a foot switch, the insufflation device is brought into a gas discharging mode. In the gas discharging mode, by performing feeding of a gas into a body cavity and discharging of a gas to the outside of the body simultaneously, a predetermined pressure is maintained in the body cavity. Gas discharging starts simultaneously with starting of gas feeding, gas discharging is finished during the gas feeding and, thereafter, gas feeding is finished. By performing gas discharging simultaneously with gas feeding, a change in pressure in the body cavity is made small.

A gas feeding amount fed from the insufflation device is set by a user. A gas feeding amount is determined based on a flow rate per unit time and a gas feeding time period. A gas feeding amount during gas feeding in intermittent gas feeding is set based on a flow rate and a time period set by the user.

On the other hand, the gas discharging amount cannot be set by a user as a gas discharging amount differs depending on ability of suction equipment or the like which a hospital has. Accordingly, the user adjusts a balance between a gas feeding amount and a gas discharging amount by setting a gas discharging time period.

SUMMARY OF THE INVENTION

According to an aspect of the present invention, an insufflation device includes: a gas feeding conduit for feeding a predetermined gas which is fed from a gas supply source into a body cavity; and a processor, wherein the processor is configured to: measure a gas feeding time period until a predetermined amount of the gas is fed according to a set pressure, measure a pressure in the body cavity; calculate a gas discharging time period based on the set pressure and a measurement result of the measured pressure; and adjust a gas feeding flow rate of the gas according to a difference between the measured gas feeding time period and the calculated gas discharging time period.

According to another aspect of the present invention, a method of adjusting an intra-abdominal pressure includes: feeding a predetermined gas which is fed from a gas supply source into a body cavity; measuring a gas feeding time period until a predetermined amount of the gas is fed according to a set pressure; measuring a pressure in the body cavity after the gas is fed into the body cavity; calculating a gas discharging time period based on the set pressure and a measurement result of the measured pressure; and adjusting a gas feeding flow rate of the gas according to a difference between the measured gas feeding time period and the calculated gas discharging time period.

DETAILED DESCRIPTION OF THE PREFERRED EMBODIMENTS

Hereinafter, embodiments of the present invention are described with reference to drawings.

First Embodiment

Figure 1:
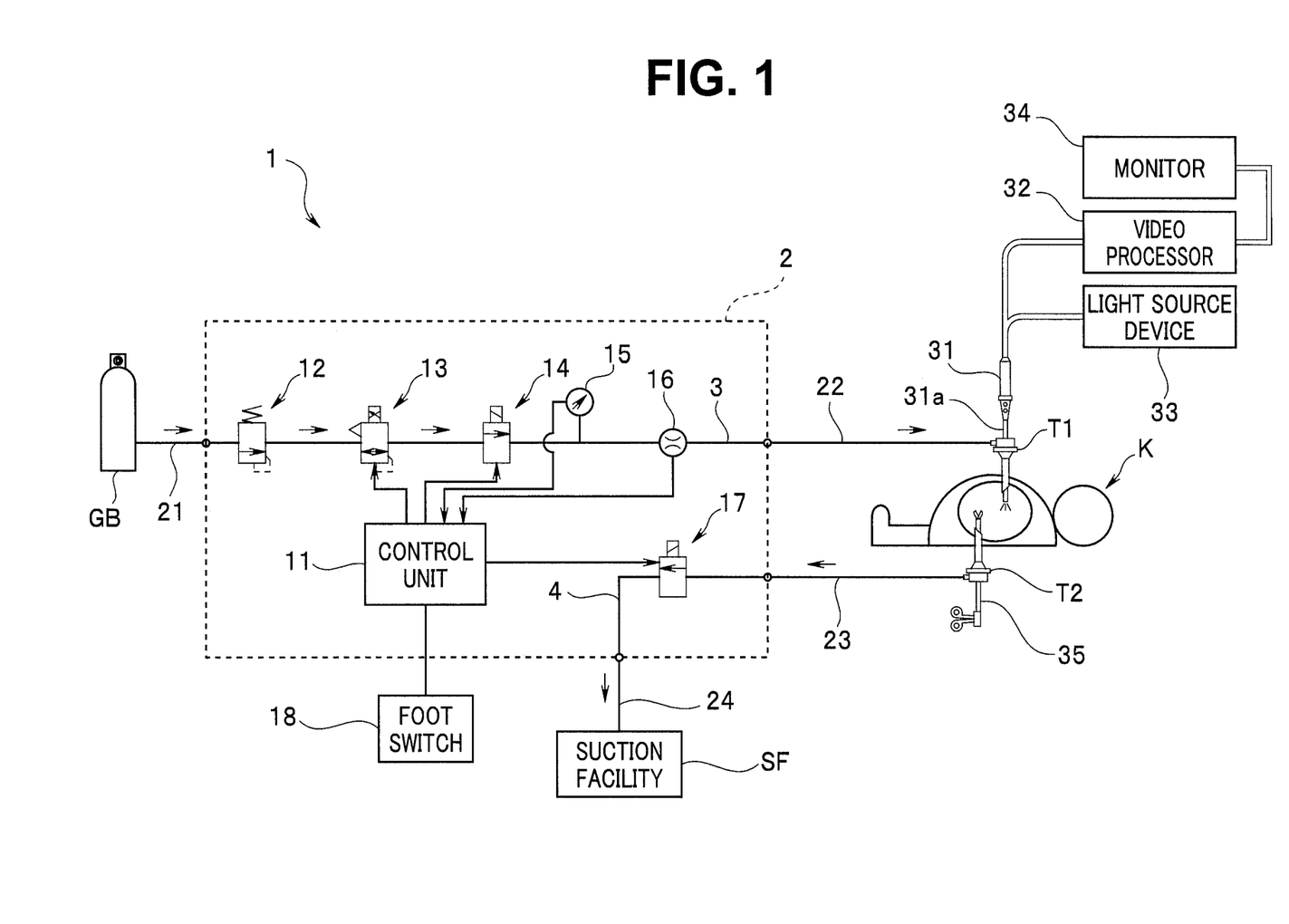
FIG. 1 is a view for describing an example of an overall configuration of a laparoscopic surgery system equipped with an insufflation device according to a first embodiment of the present invention.

FIG. 1 is a view for describing an example of an overall configuration of a laparoscopic surgery system equipped with an insufflation device according to a first embodiment of the present invention. The laparoscopic surgery system 1 shown in FIG. 1 includes an insufflation device 2. The insufflation device 2 intermittently performs gas feeding. The intermittent gas feeding is performed by alternately repeating, after gas feeding is performed, a measurement period during which gas feeding is stopped and a pressure in a body cavity is measured and a gas feeding period during which gas feeding is performed.

The insufflation device 2 adjusts a gas feeding amount and a gas discharging amount of a gas such that a pressure in a body cavity of a patient K (hereinafter, referred to as an intra-abdominal pressure) becomes a predetermined pressure. The insufflation device 2 includes a control unit 11, a pressure reducer 12, an electropneumatic regulator 13, an electromagnetic valve 14, a pressure sensor 15, a flow rate sensor 16, and an electromagnetic valve 17.

A foot switch 18 is connected to the insufflation device 2. The foot switch 18 is a device which allows a surgeon to instruct gas discharging. The foot switch 18 is connected to the control unit 11 of the insufflation device 2.

The control unit 11 is a processor for executing processing for performing various functions of the insufflation device 2. The control unit 11 includes a central processing unit (hereinafter, referred to as CPU), a ROM, a RAM and the like. Programs for performing the various functions are stored in the ROM.

The various functions are realized by the CPU reading the programs from the ROM and executing the programs.

The control unit 11 may be a processor constituted of a hardware circuit such as FPGA (field programmable gate array).

The control unit 11 is electrically connected with various devices in the insufflation device 2. The control unit 11 controls various devices in the insufflation device 2. Specifically, the control unit 11 receives signals from sensors such as the pressure sensor 15 and performs various arithmetic operations thus controlling the electropneumatic regulator 13 and the like.

A gas supply source GB, for example, a carbon dioxide gas cylinder is connected to the insufflation device 2 through a tube 21 for high pressure gas. A gas feeding tube 22 for feeding an insufflation gas such as a carbon dioxide gas into the body cavity is connected to the insufflation device 2 through a trocar T1 inserted into the abdominal cavity of a patient K.

The gas feeding tube 22 for feeding a predetermined gas fed from the gas supply source GB into the body cavity is connected to a gas feeding conduit 3.

The insufflation device 2 also includes a gas discharging conduit 4 besides the gas feeding conduit 3. The electromagnetic valve 17 is provided in the gas discharging conduit 4. A gas discharging tube 23 is connected to the insufflation device 2. The gas discharging tube 23 is a conduit which is connected to the gas discharging conduit 4, and is provided for discharging a smoke or the like in the body cavity through a trocar T2 inserted into the abdominal cavity of the patient K.

The pressure reducer 12 reduces a pressure of a high-pressure gas supplied from the gas supply source GB to a predetermined pressure. For example, the pressure of the gas supplied from the gas supply source GB at a high pressure of approximately 6 MPa is reduced to approximately 0.4 MPa.

The electropneumatic regulator 13 is an electropneumatic proportional valve which adjusts a flow rate of a gas flowing through the gas feeding conduit 3. The electropneumatic regulator 13 is a kind of an electric drive valve, and electrically adjusts a degree of opening of a valve element in multiple stages by changing a force of a pressure reducing spring which acts on the valve element. The electropneumatic regulator 13 can control a pressure reducing ratio in a variable manner by electrically adjusting the degree of opening of the valve element in multiple stages thus adjusting a gas feeding pressure to a predetermined pressure value. Based on a control signal inputted to the electropneumatic regulator 13 from the control unit 11, the electropneumatic regulator 13 changes a pressure of a carbon dioxide gas, the pressure of which is reduced by the pressure reducer 12, to a gas feeding pressure which falls within a range of approximately 3 to 10 kPa.

The electromagnetic valve 14 is a switching unit which performs opening/closing of the gas feeding conduit 3. The electromagnetic valve 14 which forms a first electromagnetic valve performs an open/close operation based on a control signal inputted from the control unit 11.

The pressure sensor 15 which forms a pressure measuring unit measures a pressure in the gas feeding conduit 3, that is, an intra-abdominal pressure. In a case where the electromagnetic valve 14 is in an open state, that is, during gas feeding, the pressure sensor 15 measures a pressure of a gas outputted from the electropneumatic regulator 13. In a case where the electromagnetic valve 14 is in a closed state (during stopping of gas feeding), the pressure sensor 15 measures an intra-abdominal pressure of a patient K through the gas feeding tube 22. A measurement result of the pressure sensor 15 is outputted to the control unit 11.

The flow rate sensor 16 measures a flow rate of a gas to be fed. In the embodiment, the flow rate sensor 16 measures a flow rate of a carbon dioxide gas per unit time supplied to the inside of the body cavity, and outputs the measurement result to the control unit 11.

The gas feeding tube 22 is a tube which introduces a gas fed from the insufflation device 2 to the trocar T1. In general, the gas feeding tube 22 is formed using a material having flexibility, and has a length of approximately 3 m.

The gas discharging tube 23 is a tube which is connected to the gas discharging conduit 4, and is provided for discharging a smoke or the like in the cavity of the patient K. The gas discharging tube 23 is a tube substantially equal to the gas feeding tube 22.

The gas discharging conduit 4 includes the electromagnetic valve 17. The electromagnetic valve 17 which forms a second electromagnetic valve is controlled by the control unit 11.

The gas discharging conduit 4 is connected to suction facility SF, which a hospital has, through a suction tube 24.

The electromagnetic valve 17 is a switching unit which performs opening/closing of the gas discharging conduit 4. The electromagnetic valve 17 performs an open/close operation based on a control signal inputted from the control unit 11. When the electromagnetic valve 17 is opened, a smoke or the like in the body cavity is sucked.

An insertion portion 31a of an endoscope 31 is insertable into the trocar T1. A video processor 32 and a light source device 33 are connected to the endoscope 31. A monitor 34 is connected to the video processor 32. An endoscope image obtained by the endoscope 31 is displayed on the monitor 34.

A treatment instrument 35 which performs cutting and removal of a living tissue in the cavity is insertable into the trocar T2.

With such a configuration, in laparoscopic surgery, a surgeon performs treatment while watching an endoscope image displayed on the monitor 34. When necessary, the surgeon can also discharge a smoke or the like in the cavity by bringing the insufflation device 2 into a gas discharging mode by stepping on the foot switch 18.

Manner of Operation

The insufflation device 2, during surgery, adjusts a gas feeding amount of a gas such that an intra-abdominal pressure of the patient K becomes a predetermined pressure. Gas feeding is intermittently performed, and measurement of the intra-abdominal pressure is performed by the pressure sensor 15 during a period between two continuous gas feeding periods. Based on the measured intra-abdominal pressure, the control unit 11 calculates a gas feeding amount for bringing the intra-abdominal pressure into a predetermined pressure. Then, the control unit 11 outputs a control signal to the electropneumatic regulator 13.

As a result, the intra-abdominal pressure during surgery can be set to a constant value and hence, a field of view of the endoscope and an operation region of the treatment instrument can be ensured.

When a smoke or the like is generated in the body cavity due to the use of the treatment instrument or the like, a surgeon can bring the insufflation device 2 into a gas discharging mode by operating the foot switch 18.

Next, the manner of operation of the insufflation device 2 during the gas discharging mode is described.

Figure 2:
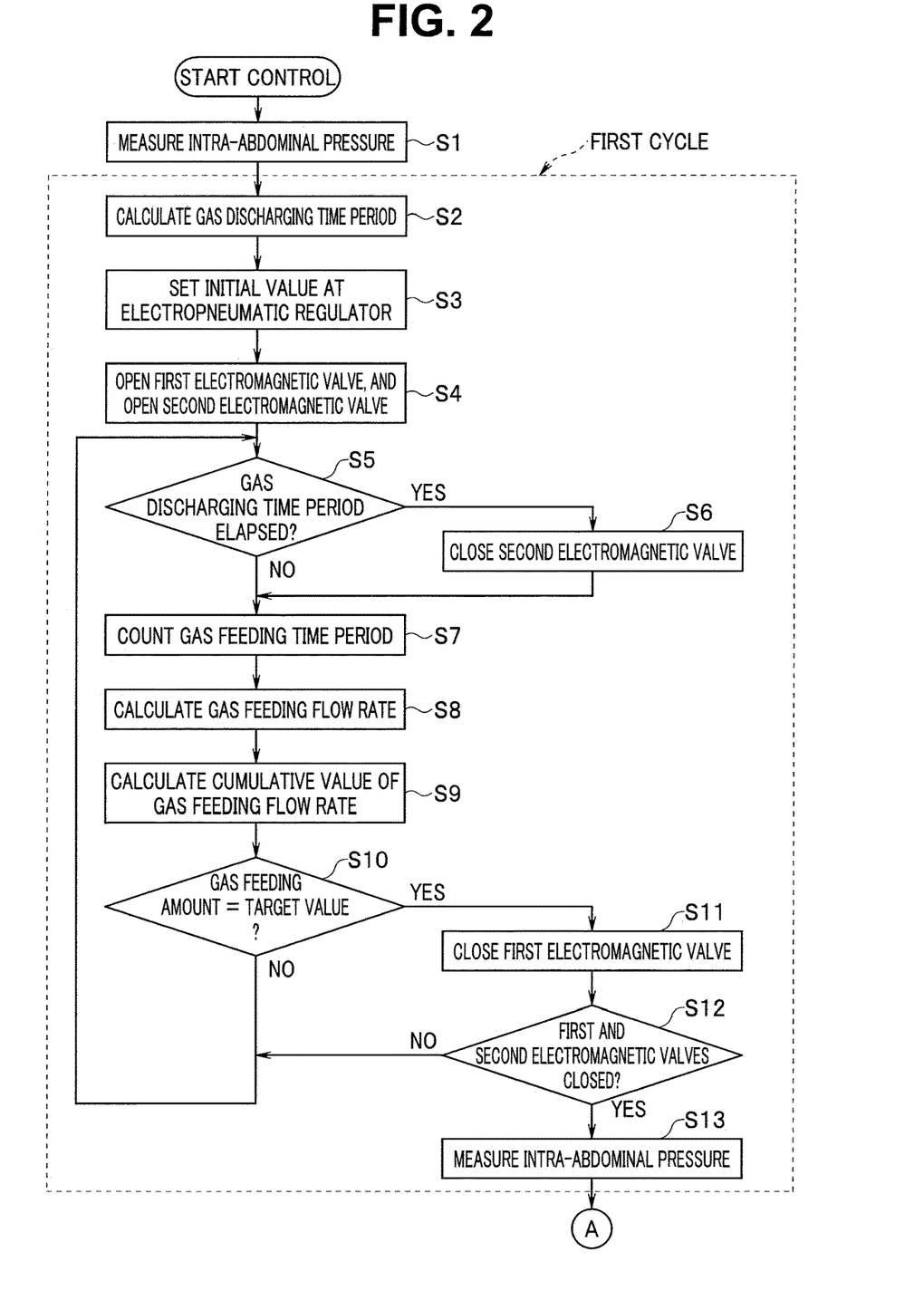
FIG. 2 is a flowchart showing an example of a flow of processing performed when a user steps on a foot switch so that the insufflation device according to the first embodiment of the present invention is brought into a gas discharging mode during a surgery.
Figure 3:
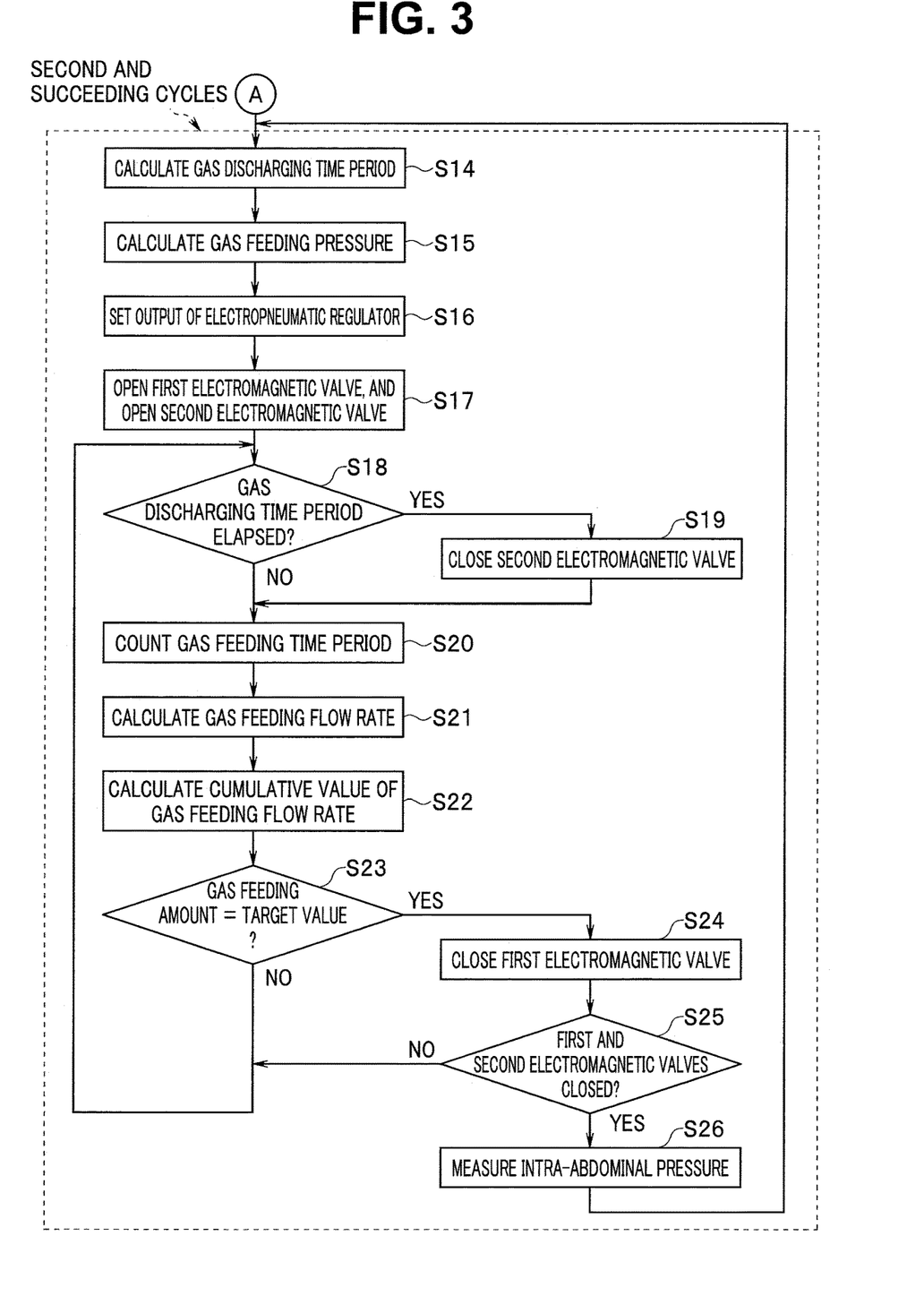
FIG. 3 is a flowchart showing an example of a flow of processing performed when a user steps on the foot switch so that the insufflation device according to the first embodiment of the present invention is brought into a gas discharging mode during a surgery.

FIG. 2 and FIG. 3 are flowcharts showing an example of a flow of processing performed when a user steps on the foot switch 18 so that the insufflation device 2 is brought into a gas discharging mode during surgery. Processing shown in FIG. 2 and FIG. 3 are performed by the control unit 11.

A gas feeding amount QS1 and a gas discharging amount QD1 in the gas discharging mode are set in advance.

The control unit 11, in the gas discharging mode, measures an intra-abdominal pressure based on an output of the pressure sensor 15 (step (hereinafter abbreviated as S) 1).

The control unit 11 calculates a gas discharging time period TE (S2). The gas discharging time period TE is calculated according to a difference between a set value of an intra-abdominal pressure set in advance by a user such as a surgeon and an intra-abdominal pressure value obtained in S1. For example, when the intra-abdominal pressure value obtained in S1 is higher than the set value, the gas discharging time period TE is set longer than the gas discharging time period set in default. When the intra-abdominal pressure value obtained in S1 is lower than the set value, the gas discharging time period TE is adjusted and calculated such that the gas discharging time period TE becomes shorter than the gas discharging time period set in default.

For example, assuming sp as a set value, pv as an intra-abdominal pressure value, x1 as an initial value, and α as a coefficient, the gas discharging time period TE is calculated by a following equation (1).

$$TE = \alpha \times (sp - pv) + x1 \tag{1}$$

After S2 is finished, the control unit 11 sets an output of the electropneumatic regulator 13 such that a gas feeding pressure becomes an initial value x2 (S3). In other words, in a first cycle C1 in a gas discharging mode, the output of the electropneumatic regulator 13 is set such that the gas feeding pressure becomes the initial value x2. As a result, the electropneumatic regulator 13 supplies a gas to the gas feeding conduit 3 at the gas feeding pressure of the set initial value x2.

Target values QD of the gas feeding amounts in respective cycles in the gas discharging mode are set in advance by the user.

After S3 is finished, the control unit 11 transmits a control signal to the electromagnetic valves 14 and 17 so as to open the electromagnetic valve 14 which forms the first electromagnetic valve and the electromagnetic valve 17 which forms the second electromagnetic valve (S4).

After S4 is finished, the control unit 11 determines whether or not the gas discharging time period TE calculated in S2 has elapsed (S5).

When the gas discharging time period TE has elapsed (S5: YES), the control unit 11 closes the electromagnetic valve 17 which forms the second electromagnetic valve (S6).

When the gas discharging time period TE has not elapsed (S5: NO), the control unit 11 counts a gas feeding time period TS by incrementing a counter (S7). Accordingly, the process in S7 constitutes a gas feeding time period measuring unit which measures a gas feeding time period until a predetermined amount of gas is fed according to a set value sp which is a set pressure.

After S7 is finished, the control unit 11 calculates a gas feeding flow rate based on an output of the flow rate sensor 16 (S8).

After S8 is finished, the control unit 11 calculates a cumulative value of the gas feeding flow rate, that is, a cumulative flow rate (S9). The cumulative flow rate is a cumulative value from a time point t0. The cumulative flow rate is calculated by multiplying the gas feeding time period TS obtained from the count value in S7 by the gas feeding flow rate per unit time detected in S8.

The control unit 11 determines whether or not the cumulative flow rate calculated in S9 becomes a target value QD (S10).

In step S10, when the cumulative flow rate becomes the target value QD (S10: YES), the control unit 11 closes the electromagnetic valve 14 which forms the first electromagnetic valve (S11).

After S11 is finished, the control unit 11 determines whether or not both the first and second electromagnetic valves are closed (S12).

When both the electromagnetic valves 14 and 17 are closed, an intra-abdominal pressure is measured by the pressure sensor (S13), and the first cycle is finished.

When the gas discharging time period TE is longer than the gas feeding time period TS, there is a case where the electromagnetic valve 17 is in an open state although the electromagnetic valve 14 is closed. In this case, both the electromagnetic valves 14 and 17 are not closed and hence, a determination in S12 becomes NO and processing returns to S5, and when the gas discharging time period TE has elapsed, the electromagnetic valve 17 is closed. As a result, the determination in S12 becomes YES.

When the cumulative flow rate does not become the target value QD (S10: YES) and both the first and second electromagnetic valves are not closed (S12: NO), processing returns to S5.

An intra-abdominal pressure in the first cycle, and timing of gas feeding and timing of gas discharging are described.

Figure 4:
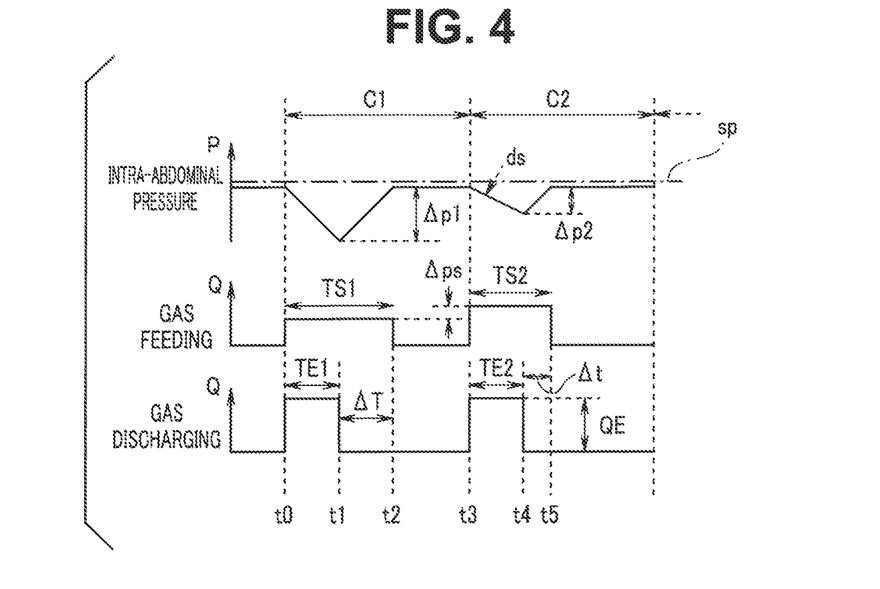
FIG. 4 is a graph relating the first embodiment of the present invention showing a change in pressure in a body cavity and timing of gas feeding and timing of gas discharging after the gas discharging mode starts.

FIG. 4 is a graph showing a change in intra-abdominal pressure and timing of gas feeding and timing of gas discharging after the gas discharging mode starts.

In the gas discharging mode, the electromagnetic valves 14 and 17 open at timing of a time point t0 shown in FIG. 4 (S4).

When the electromagnetic valve 17 is opened, lowering of the intra-abdominal pressure starts. When a gas discharging time period TE1 has elapsed and timing of a time point t1 comes, the electromagnetic valve 17 is closed (S6).

Since gas feeding is performed until a cumulative value of a gas feeding flow rate becomes a target value QD, rising of intra-abdominal pressure starts. When the cumulative value of the gas feeding flow rate becomes a target value, the electromagnetic valve 14 is closed, and a gas feeding time period TS1 in the first cycle C1 is finished.

In FIG. 4, the electromagnetic valve 14 is closed at timing of a time point t2. A time difference between time points t1 and t2 is ΔT. In other words, ΔT is a difference between the gas feeding time period TS1 and the gas discharging time period TE1.

As shown in FIG. 3, the control unit 11 calculates the gas discharging time period TE based on the intra-abdominal pressure measured in S13 (S14). A method of calculating the gas discharging time period TE in S14 is equal to the method used in S2.

Accordingly, the process in S14 constitutes the gas discharging time period calculation unit which calculates the gas discharging time period TE based on a set value sp of a set pressure and a measurement result of a pressure measured by the pressure sensor 15.

After S14 is finished, the control unit 11 calculates a gas feeding pressure according to a difference between the gas feeding time period TS counted in S7 and the gas discharging time period TE calculated in S14 (S15). In other words, the process in S15 constitutes a pressure measuring unit which is provided in the gas feeding conduit 3 and measures a pressure in a body cavity.

For example, assuming x2 as an initial value and β as a coefficient, a gas feeding pressure Ps is calculated by a following equation (2).

$$Ps = \beta \times \Delta T + x2 \quad (2)$$

The control unit 11 sets an output of the electropneumatic regulator 13 such that the gas feeding pressure calculated in S15 is obtained (S16).

In other words, the control unit 11, when the insufflation device 2 is brought into a gas discharging mode where gas discharging is performed, adjusts the gas feeding flow rate of a gas based on a gas discharging time period and a gas feeding time period during a first measurement period.

As described above, the control unit 11, in the processes in S14 to S16, adjusts the gas feeding flow rate of a gas according to a difference between the gas feeding time period TS measured in S7 and the gas discharging time period TE calculated in S14.

The control unit 11 adjusts the gas feeding flow rate of the gas as follows. The gas feeding flow rate is increased when the gas feeding time period TS is longer than the gas discharging time period TE, and the gas feeding flow rate is decreased when the gas feeding time period TS is shorter than the gas discharging time period TE.

In FIG. 4, the gas feeding flow rate in a cycle C2 is larger than the gas feeding flow rate in the cycle C1 by Δps.

After S16 is finished, the control unit 11 performs processes in S17 to S26 shown in FIG. 3. The processes in S17 to S26 in FIG. 3 are equal to the processes in S4 to S13 in FIG. 2 respectively and hence, a description of the processes in S17 to S26 is omitted.

Also in the cycle C2, there is a case where a difference Δt is generated between a gas feeding time period TS2 and a gas discharging time period TE2. Accordingly, after S26 shown in FIG. 3 is finished, the processing returns to S14, and an operation substantially equal to the operation in the second cycle is performed also in third and succeeding cycles until Δt becomes 0 or a predetermined value or below.

As shown in FIG. 4, in the second cycle C2, an output of the electropneumatic regulator 13 is set such that the gas feeding pressure calculated in S15 is obtained (S16) and hence, a gas feeding amount is increased by Δps.

A target value of the gas feeding amount in the gas discharging mode is set in advance and hence, also in the second cycle, when the gas feeding amount becomes the target value in S10, gas feeding is stopped. The gas feeding amount is increased by Δps, the gas feeding time period TS2 in the second cycle becomes shorter than the gas feeding time period TS1 in the preceding cycle C1.

As a result, as shown in FIG. 4, a lowering gradient ds of the intra-abdominal pressure after gas feeding starts in the cycle C2 becomes gentle, and a lowering amount Δp2 of the intra-abdominal pressure in the cycle C2 becomes smaller than a lowering amount Δp1 of the intra-abdominal pressure in the preceding cycle C1.

Accordingly, in the intermittent gas feeding, a change in intra-abdominal pressure is suppressed in the gas discharging mode.

Figure 5:
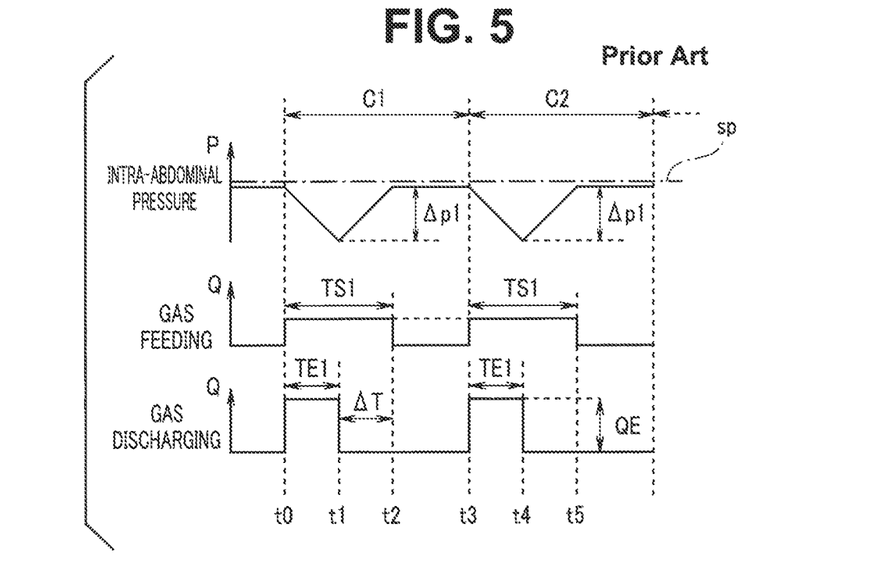
FIG. 5 is a graph relating to the first embodiment of the present invention showing a change in pressure in the body cavity and timing of gas feeding and timing of gas discharging after the gas discharging mode starts in a case where processing according to the first embodiment is not performed.

FIG. 5 is a graph showing a change in intra-abdominal pressure and timing of gas feeding and timing of gas discharging after the gas discharging mode starts in a case where processing according to the embodiment is not performed.

As shown in FIG. 5, in the second and succeeding cycles, a gas feeding pressure does not change and hence, a change in intra-abdominal pressure is not suppressed.

As described above, according to the above-mentioned embodiment, it is possible to provide the insufflation device and the method of adjusting an intra-abdominal pressure which suppress a change in intra-abdominal pressure when gas feeding and gas discharging are performed simultaneously.

Second Embodiment

In the first embodiment, a gas feeding pressure in the next cycle is increased according to a difference between a gas feeding time period and a gas discharging time period, and a gas feeding flow rate per unit time is increased thus suppressing a change in intra-abdominal pressure in the gas discharging period. However, the gas feeding pressure has an upper limit and a lower limit and hence, there is a case where a change in intra-abdominal pressure cannot be suppressed.

The present embodiment relates to an insufflation device which can suppress a change in intra-abdominal pressure even when such a gas feeding pressure has an upper limit and a lower limit.

A configuration of the insufflation device according to the present embodiment is equal to a configuration of the insufflation device according to the first embodiment shown in FIG. 1 and hence, the description of the insufflation device according to the present embodiment is omitted. Hereinafter, with respect to the insufflation device according to the second embodiment, a flow of processing in a gas discharging mode which differs from the corresponding flow of the processing in the first embodiment is described.

Processing in a first cycle is equal to the processing shown in FIG. 2 in the first embodiment. Processing in second and succeeding cycles in the present embodiment differ from the processing shown in FIG. 3 in the first embodiment.

Figure 6:
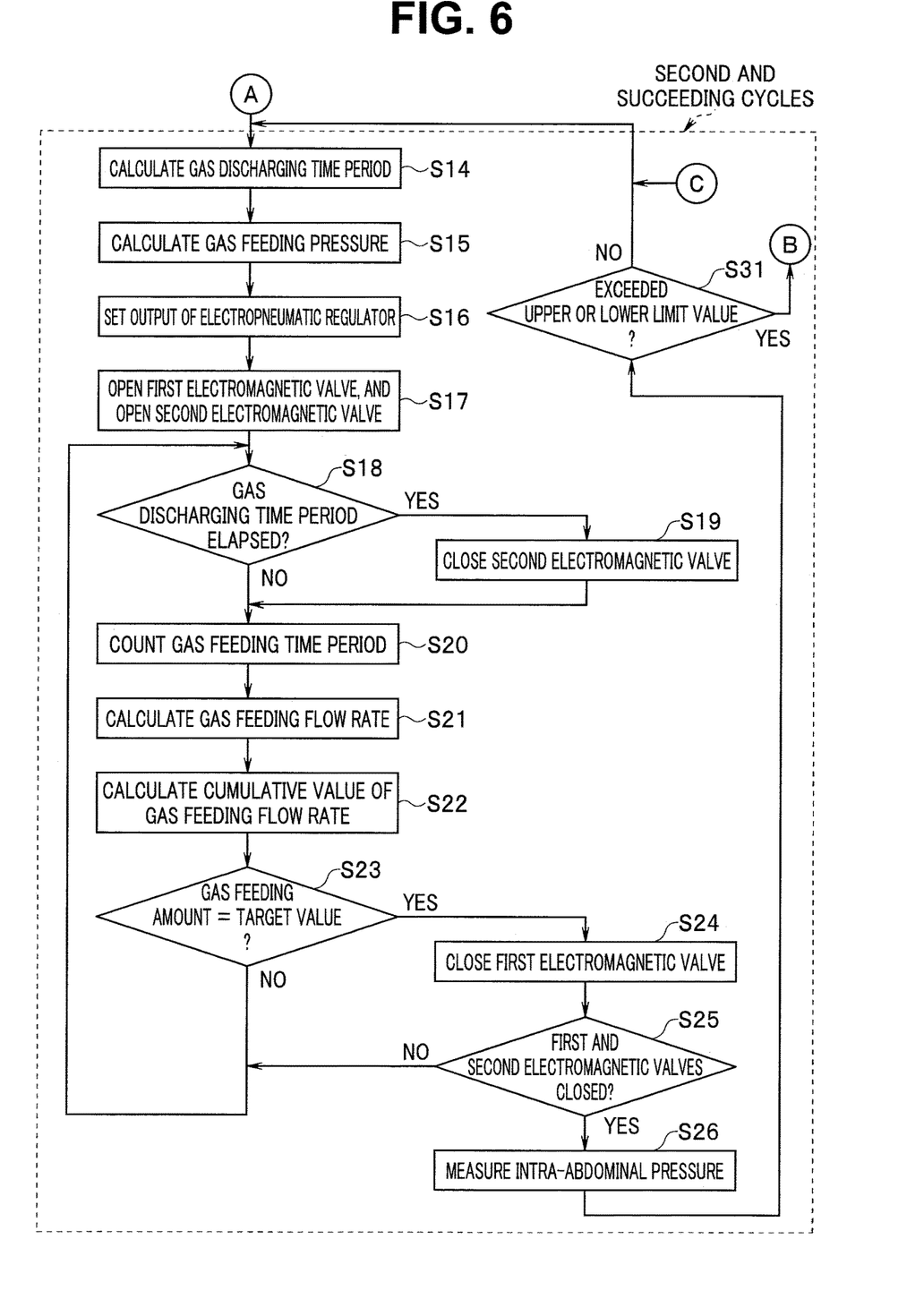
FIG. 6 is a flowchart showing an example of a flow of processing performed when a user steps on a foot switch so that an insufflation device according to a second embodiment of the present invention is brought into a gas discharging mode during a surgery.
Figure 7:
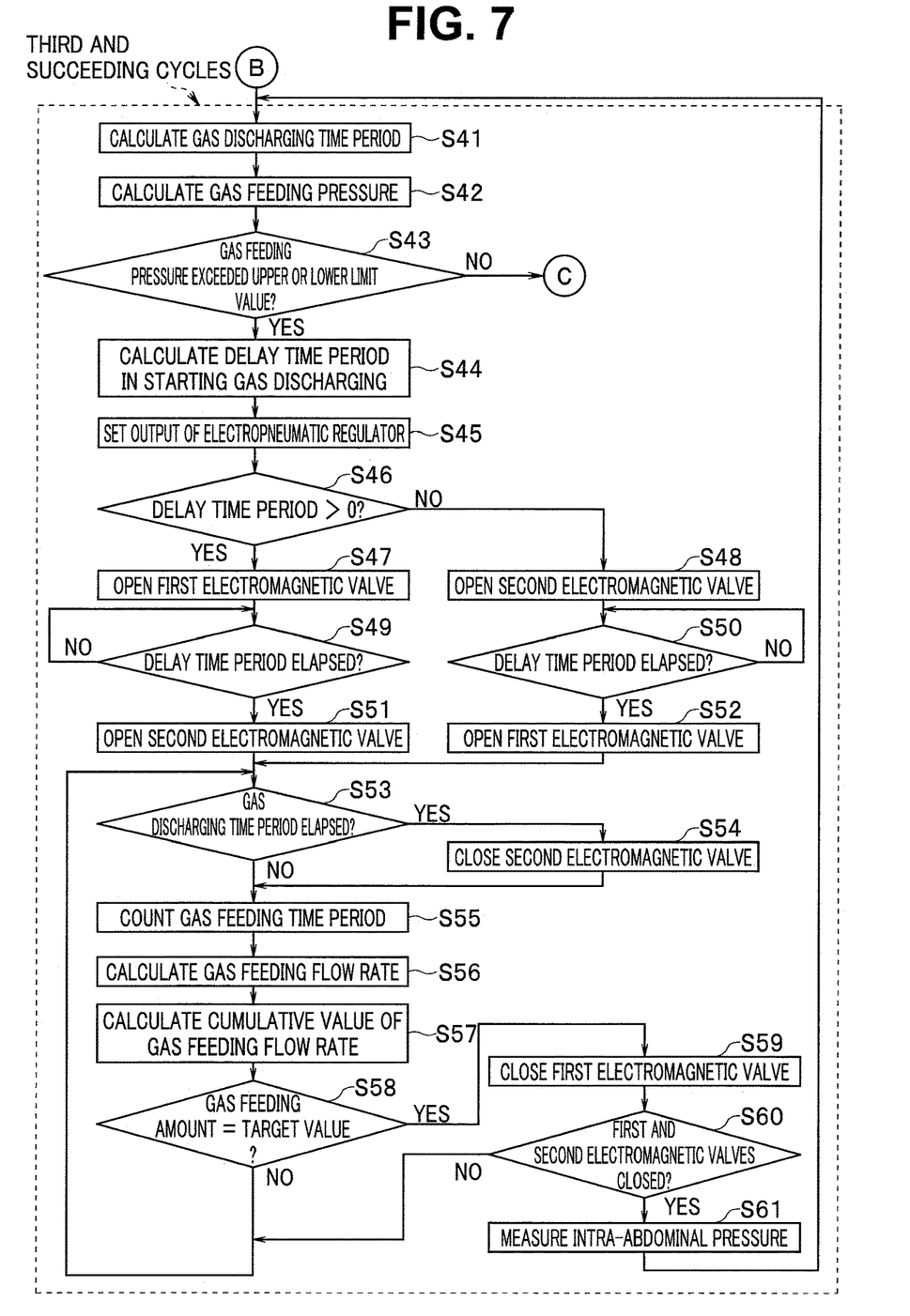
FIG. 7 is a flowchart showing an example of a flow of processing performed when a user steps on the foot switch so that the insufflation device according to the second embodiment of the present invention is brought into a gas discharging mode during a surgery.

In FIG. 6 and FIG. 7, processes which are equal to the processes in steps shown in FIG. 2 and FIG. 3 in the first embodiment are given with step numbers shown in FIG. 2 and FIG. 3 and the description of the processes is omitted.

FIG. 6 and FIG. 7 are flowcharts showing an example of a flow of processing performed when a user steps on the foot switch 18 so that the insufflation device 2 is brought into a gas discharging mode during a surgery. The processing shown in FIG. 6 and FIG. 7 are performed by the control unit 11.

Next, the manner of operation of the insufflation device 2 in the gas discharging mode is described.

Also in the present embodiment, during a surgery, when a user steps on the foot switch 18 so that the insufflation device 2 is brought into a gas discharging mode, processing shown in FIG. 2 which is described in the first embodiment is performed first. In this manner, the processing in the first cycle C1 is equal to the processing in the first embodiment and hence, the description of the processing is omitted.

When the processing in the second cycle C2 starts, the control unit 11 performs the processing shown in FIG. 6 and FIG. 7.

FIG. 6 and FIG. 7 are flowcharts showing the example of the flow of the processing in the second and succeeding cycles. Processing shown in FIG. 6 and FIG. 7 are performed by the control unit 11.

The processing in FIG. 6 is equal to the processing shown in FIG. 3. However, the processing shown in FIG. 6 differs from the processing shown in FIG. 3 with respect to a point that a process S31 is added. Processes S14 to S26 shown in FIG. 6 are equal to the processes in S14 to S26 shown in FIG. 3 and hence, the description of the processes is omitted.

In S26, after an intra-abdominal pressure is measured, the control unit 11 determines whether or not a gas feeding pressure exceeds an upper or lower limit value (S31). When the gas feeding pressure exceeds the upper limit value or the lower limit value (S31: YES), the processing shown in FIG. 7 is performed.

In FIG. 7, the control unit 11 calculates a gas discharging time period based on an intra-abdominal pressure measured in S26 (S41).

Then, the control unit 11 calculates a gas feeding pressure according to a difference between a gas feeding time period counted in S20 and the gas discharging time period calculated in S41 (S42).

The control unit 11 determines whether or not the gas feeding pressure exceeds the upper or lower limit value (S43). In other words, the control unit 11 determines whether or not the gas feeding pressure set by the electropneumatic regulator 13 exceeds the upper limit value or exceeds the lower limit value.

When the gas feeding pressure exceeds the upper or lower limit value (S43: YES), the control unit 11 calculates a delay time period dx of timing of starting gas discharging (S44).

The delay time period dx of timing of starting gas discharging is calculated by a following equation (3), for example.

$$dx = \Delta T/2 \qquad (3)$$

In other words, a half of a difference between the gas feeding time period TS and the gas discharging time period TE becomes the delay time period dx.

When the delay time period dx takes a positive value, such a condition means that the gas feeding pressure reaches the upper limit value and a gas feeding amount cannot be increased any more.

When the delay time period dx takes a negative value, such a condition means that the gas feeding pressure reaches the lower limit value and the gas feeding amount cannot be decreased any more.

The delay time period dx is set in a predetermined counter as a delay count value corresponding to the delay time period dx and, thereafter, the delay count value is decreased along with a lapse of time during the cycle. When the delay time period dx has not elapsed from a time point that gas feeding starts, the delay count value is larger than 0. When the delay time period dx has elapsed from the time point that gas feeding starts, the delay count value becomes 0 or below.

Next, the control unit 11 performs setting of an output of the electropneumatic regulator 13 (S45). When the gas feeding pressure exceeds the upper limit value, the output of the electropneumatic regulator 13 is set to an output by which the gas feeding pressure agrees with the upper limit value of gas feeding. When the gas feeding pressure exceeds the lower limit value, the output of the electropneumatic regulator 13 is set to an output by which the gas feeding pressure agrees with the lower limit value of gas feeding.

Next, the control unit 11 determines whether or not the delay time period dx exceeds 0 (S46).

When the delay time period dx exceeds 0 (S46: YES), the control unit 11 opens the electromagnetic valve 14 which forms the first electromagnetic valve (S47). In other words, when the delay time period dx is a positive value (S46: YES), the electromagnetic valve 14 is opened, and gas feeding is performed prior to gas discharging.

When the delay count value does not exceed 0 (S46: NO), the control unit 11 opens the electromagnetic valve 17 which forms the second electromagnetic valve (S48). In other words, when the delay count value is a negative value (S46:

NO), the electromagnetic valve 17 is opened, and gas discharging is performed prior to gas feeding.

After S47 is finished, the control unit 11 determines whether or not the delay time period dx for starting gas discharging has elapsed (S49). When the delay time period dx for starting gas discharging has elapsed (S49: YES), the control unit 11 opens the electromagnetic valve 17 (S51) thus starting gas discharging.

After S48 is finished, the control unit 11 determines whether or not the delay time period dx for starting gas discharging has elapsed (S50). When the delay time period dx for starting gas discharging has elapsed (S50: YES), the control unit 11 opens the electromagnetic valve 14 (S52) thus starting gas feeding.

The electromagnetic valve 17 or 14 does not open until the delay time period dx for starting gas discharging has elapsed.

As described above, the processes in S44 to S52 constitute a start timing adjusting unit which adjusts timing of starting the gas feeding time period and timing of starting the gas discharging time period. The control unit 11 shifts timing of starting the gas feeding time period or timing of starting the gas discharging time period by the adjusted timing.

After S51 and S52 are finished, processes in S53 to S61 are performed. The processes in S53 to S61 shown in FIG. 7 are equal to the processes in S18 to S26 shown in FIG. 3 in the first embodiment. In other words, the electromagnetic valve 17 is in an open state until the gas discharging time period TE has elapsed, and the electromagnetic valve 17 is closed when the gas discharging time period TE has elapsed (S54).

The electromagnetic valve 14 is in an open state until a gas feeding amount becomes a target value, and the electromagnetic valve 14 is closed when the gas feeding amount becomes the target value (S59).

When both the electromagnetic valves 14 and 17 are closed (S60: YES), the control unit 11 measures an intra-abdominal pressure based on an output of the pressure sensor 15, and the processing returns to S41.

In the third and succeeding cycles, when the gas feeding pressure exceeds an upper or lower limit value (S43: YES), the control unit 11 performs processes in S44 and succeeding steps.

In the third and succeeding cycles, when the gas feeding pressure does not exceed the upper or lower limit value (S43: NO), the processing returns to S14 shown in FIG. 6.

Figure 8:
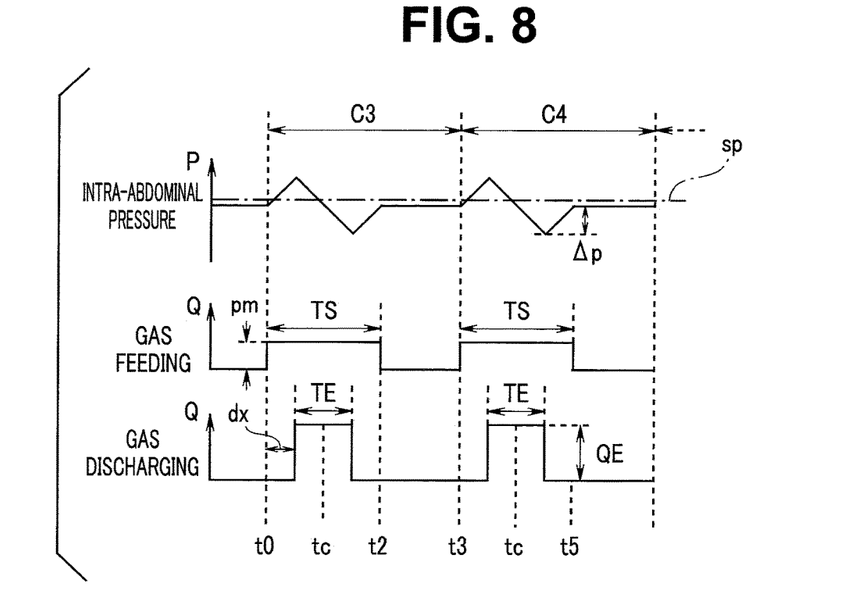
FIG. 8 is a graph relating to the second embodiment of the present invention showing a change in pressure in a body cavity and timing of gas feeding and timing of gas discharging in a case where a gas feeding pressure exceeds an upper limit value so that gas discharging starts with a delay by a delay time period.

FIG. 8 is a graph showing a change in intra-abdominal pressure and timing of gas feeding and timing of gas discharging in a case where the gas feeding pressure exceeds the upper limit value so that gas discharging starts with a delay by the delay time period dx.

As shown in FIG. 8, in the third and succeeding cycles, the gas feeding pressure does not change and hence, a change in intra-abdominal pressure is not suppressed. Since the gas feeding pressure reaches the upper limit value, the gas feeding flow rate takes a maximum value pm.

However, since the delay time period dx is set, starting of gas discharging is delayed by the delay time period dx.

The delay time period dx is calculated such that gas discharging is performed just at a center of the gas feeding period based on the above-mentioned equation (3).

Accordingly, the intra-abdominal pressure P rises immediately after starting gas feeding, becomes larger than a set value sp, and is lowered when gas discharging starts. Gas discharging is performed in a middle of the gas feeding period and hence, a change in intra-abdominal pressure P occurs upward and downward with respect to a set value sp. Accordingly, a deviation amount $\Delta p$ of the intra-abdominal pressure P from the set value sp is small.

Particularly, based on the equation (3), timing which is a half of the gas discharging period agrees with timing at a time point tc at the center of the gas feeding period and hence, the deviation amount $\Delta p$ of the intra-abdominal pressure P from the set value sp takes a minimum value.

In other words, when the gas feeding time period TS and the gas discharging time period TE do not agree with each other, the control unit 11 adjusts timing of starting the gas feeding time period TS or timing of starting the gas discharging time period TE such that timing of the half of the gas discharging time period TE agrees with the timing of a half of the gas feeding time period TS.

FIG. 8 shows the case where the gas feeding pressure exceeds the upper limit value. On the other hand, when the gas feeding pressure exceeds the lower limit value, gas feeding is performed in the middle of the gas discharging period. Accordingly, a change in intra-abdominal pressure P occurs upward and downward with respect to the set value sp and hence, a deviation amount $\Delta p$ of the intra-abdominal pressure P from the set value sp is small.

As described above, according to the above-mentioned embodiment, it is possible to provide the insufflation device and the method of adjusting an intra-abdominal pressure which suppress a change in intra-abdominal pressure when gas feeding and gas discharging are performed simultaneously.

In the first and the second embodiments, unless the gas discharging tube 23 is properly connected to the insufflation device 2, discharging of a gas in the body cavity is not properly performed. Accordingly, processing for checking a connection state of the gas discharging tube 23 is performed.

Before the treatment starts, the control unit 11 performs the following processing for checking the connection of the gas discharging tube 23.

The control unit 11 opens the electromagnetic valve 17, measures an intra-abdominal pressure at a predetermined timing, and calculates a gradient of lowering of the intra-abdominal pressure.

Figure 9:
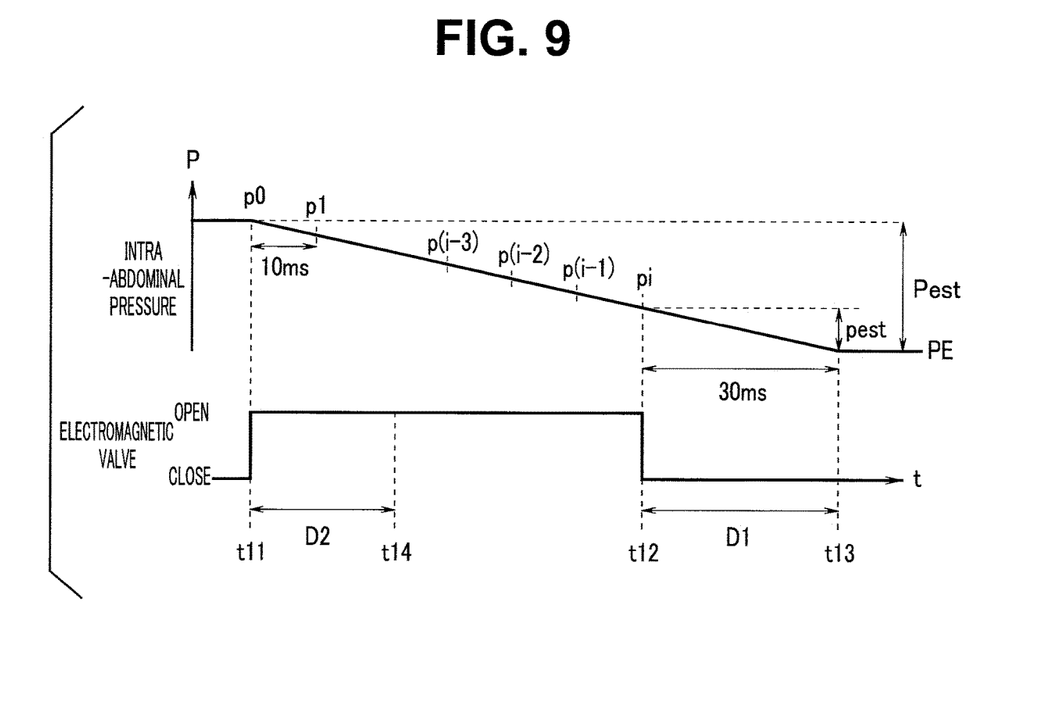
FIG. 9 is a graph showing a change in pressure in a body cavity at the time of checking connection of a gas discharging tube.

FIG. 9 is a graph showing a change in intra-abdominal pressure at the time of checking connection of the gas discharging tube 23.

When the control unit 11 sets an intra-abdominal pressure P to a predetermined pressure p0 by opening the electromagnetic valve 14, and, thereafter, opens the electromagnetic valve 17 at a time point t0, the intra-abdominal pressure P starts lowering as shown in FIG. 9.

The control unit 11 measures the intra-abdominal pressure P at a predetermined cycle based on a signal from the pressure sensor 15. The predetermined cycle is 10 ms (milliseconds) in this embodiment.

When the gas discharging tube 23 is correctly connected to the insufflation device 2, after the electromagnetic valve 17 is opened, the intra-abdominal pressure P becomes a predetermined pressure value after a lapse of a predetermined period. However, when the gas discharging tube 23 is not correctly connected to the insufflation device 2, after the electromagnetic valve 17 is opened, the intra-abdominal pressure P becomes the predetermined pressure value or below before a lapse of the predetermined period.

Accordingly, the control unit 11 can determine whether or not the gas discharging tube 23 is correctly connected to the insufflation device 2 based on the elapsed time period after the electromagnetic valve 17 is opened and the intra-abdominal pressure P.

Although the control unit 11 closes the electromagnetic valve 17 when the intra-abdominal pressure P becomes a predetermined pressure, the electromagnetic valve 17 has a delay from a time point that the electromagnetic valve 17 receives a close control signal to a time point that the electromagnetic valve 17 is completely closed. In other words, the electromagnetic valve 17 has a close delay.

Accordingly, even when the control unit 11 outputs a control signal for closing the electromagnetic valve 17 after the intra-abdominal pressure P becomes a predetermined pressure PE, the intra-abdominal pressure P becomes lower than the predetermined pressure PE due to the close delay. When the intra-abdominal pressure P is lowered more than necessary, a change in an operation field is increased.

In view of such circumstances, in the embodiments, the control unit 11 estimates a time period that the intra-abdominal pressure P becomes the predetermined pressure PE based on a change with time of the intra-abdominal pressure P by taking into account a close delay, and outputs a close control signal to the electromagnetic valve 17 before the intra-abdominal pressure P becomes the predetermined pressure.

As a result, there is no possibility that the intra-abdominal pressure P is lowered more than necessary.

As shown in FIG. 9, the control unit 11 measures the intra-abdominal pressure P at a predetermined cycle, and estimates a lowering amount pest of the intra-abdominal pressure P based on a following equation (4).

In the embodiments, assume a close delay of the electromagnetic valve 17 as 30 ms. Accordingly, the lowering amount pest of the intra-abdominal pressure P which is estimated by taking into account the close delay is calculated by the equation (4).

$$\text{pest}=(p(i-3)-p(i-2))+((p(i-3)-p(i-1))/2)+((p(i-3)-pi))/3) \quad (4)$$

Wherein, pi is an intra-abdominal pressure measured at a current time point, p(i−1) is the intra-abdominal pressure measured at one preceding time point counted from the current time point, p(i−2) is the intra-abdominal pressure measured at two preceding time point counted from the current time point, and p(i−3) is the intra-abdominal pressure measured at three preceding time point counted from the current time point.

A predetermined pressure Pest is a pressure which the intra-abdominal pressure is scheduled to reach after a lapse of a predetermined period by opening the electromagnetic valve 17 for checking the connection of the gas discharging tube 23, and is a preset value.

The control unit 11 estimates the lowering amount pest by the above-mentioned equation (4) at a predetermined cycle (for every 10 ms in the embodiments).

Then, the control unit 11 determines whether or not a following equation (5) is satisfied.

$$\text{Pest}=\text{pest}+(p0-pi) \quad (5)$$

Pest is a difference between the predetermined pressure PE and an intra-abdominal pressure p0 before the electromagnetic valve 17 is opened.

When the equation (5) is satisfied, as shown in FIG. 9, the intra-abdominal pressure P becomes the predetermined pressure PE after the close delay (30 ms in the embodiments) and hence, the control unit 11 outputs a close control signal to the electromagnetic valve 17 at a time point t12 by taking into account a close delay D1 of the electromagnetic valve 17. As a result, the intra-abdominal pressure P becomes the predetermined pressure PE at a time point t13 which comes after the time point t12 by the close delay D1 and hence, the intra-abdominal pressure P is not lower than the predetermined pressure PE.

In FIG. 9, D2 indicates an open delay of the electromagnetic valve 17.

Accordingly, by performing the above-mentioned processing, the intra-abdominal pressure P is not lowered more than necessary for checking the connection state of the gas discharging tube 23 and hence, a large change in an operation field can be obviated.

The present invention is not limited to the above-mentioned embodiments, and various changes and modifications are conceivable without departing from the gist of the present invention.

What is claimed is:

1. A control apparatus comprising,
a processor comprising hardware, the processor being configured to:
acquire a first gas feeding time period in a first cycle and a first gas discharging time period in the first cycle in which gas is fed into a body cavity and gas is discharged from the body cavity, respectively; and
adjust a first gas feeding amount per unit time during gas feeding in a second cycle after the first cycle, based on the acquired first gas feeding time period and the acquired first gas discharging time period.

2. The control apparatus according to claim 1, wherein the adjusting of the first gas feeding amount per unit time comprises adjusting the first gas feeding amount per unit time such that a first difference between a second gas feeding time period in the second cycle and a second gas discharging time period in the second cycle becomes smaller than a second difference between the first gas feeding time period and the first gas discharging time period.

3. The control apparatus according to claim 1, wherein the adjusting of the first gas feeding amount per unit time comprises increasing the first gas feeding amount per unit time such that a second gas feeding time period in the second cycle is shorter than the first gas feeding time period.

4. The control apparatus according to claim 1, wherein the processor is configured to acquire a pressure in the body cavity.

5. The control apparatus according to claim 4, wherein
the processor is configured to calculate the first gas discharging time period based on the acquired pressure in the body cavity; and
the acquired pressure in the body cavity is acquired in a period that a gas feeding and a gas discharging are not performed.

6. The control apparatus according to claim 1, wherein the processor is configured to receive the first gas feeding time period and the first gas discharging time period as an input from an operator.

7. The control apparatus according to claim 6, wherein the processor is configured to:
acquire a second gas feeding time period in the second cycle and a second gas discharging time period in the second cycle, and
adjust a second gas feeding amount per unit time during gas feeding in a third cycle after the second cycle, based on the acquired second gas feeding time period and the acquired second gas discharging time period.

8. The control apparatus according to claim 7, wherein the processor is configured to repeat the adjusting of the second gas feeding amount per unit time until a difference between the second gas feeding time period and the second gas discharging time period becomes a predetermined value or below.

9. The control apparatus according to claim 1, wherein the processor is configured to change a timing of a start of gas fed or gas discharged in the second cycle, based on the first gas feeding time period and the first gas discharging time period.

10. The control apparatus according to claim 9, wherein the processor is configured to determine whether the first gas feeding amount per unit time reaches one of a set upper limit value or a set lower limit value,
wherein the changing of the timing comprises changing the timing when the first gas feeding amount per unit time reaches the upper limit value or the lower limit value.

11. The control apparatus according to claim 9, wherein the processor is configured to:
set a second gas feeding period in the second cycle prior to a second gas discharging period in the second cycle when the first gas feeding time period is longer than the first gas discharging time period, and
set the second gas feeding period after the second gas discharging period when the first gas feeding time period is shorter than the first gas discharging time period.

12. The control apparatus according to claim 9, wherein the processor is configured to calculate a delay time period based on a difference between the first gas feeding time period and the first gas discharging time period,
wherein the changing of the timing comprises changing the timing based on the delay time period.

13. The control apparatus according to claim 1, wherein the first cycle is a period from a start of a gas feeding at a gas feeding amount set by an operator until a start of a gas feeding in the second cycle.

14. A method of adjusting an intra-abdominal pressure, the method comprising:
acquiring, via a processor, a first gas feeding time period in a first cycle and a first gas discharging time period in the first cycle in which gas is fed into a body cavity and gas is discharged from the body cavity, respectively; and
adjusting, via the processor, a gas feeding amount per unit time during gas feeding in a second cycle after the first cycle, based on the acquired first gas feeding time period and the acquired first gas discharging time period.

15. The method of adjusting the intra-abdominal pressure according to claim 14, wherein the adjusting comprises, adjusting, via the processor, the gas feeding amount per unit time such that a first difference between a second gas feeding time period in the second cycle and a second gas discharging time period in the second cycle becomes smaller than a second difference between the first gas feeding time period and the first gas discharging time period.

16. The method of adjusting the intra-abdominal pressure according to claim 15, wherein the adjusting of the gas feeding amount per unit time comprises increasing, via the processor, the gas feeding amount per unit time such that the second gas feeding time period is shorter than the first gas feeding time period.

17. An insufflation device comprising:
a valve configured to control a supply of a gas into a body cavity; and
a processor configured to control the valve, the processor being configured to:
acquire a first gas feeding time period in a first cycle and a first gas discharging time period in the first cycle in which gas is fed into a body cavity and gas is discharged from the body cavity, respectively; and
adjust a gas feeding amount per unit time during gas feeding in a second cycle after the first cycle, based on the acquired first gas feeding time period and the acquired first gas discharging time period.

18. The insufflation device according to claim 17, wherein the adjusting of the gas feeding amount per unit time comprises adjusting the gas feeding amount per unit time such that a first difference between a second gas feeding time period in the second cycle and a second gas discharging time period in the second cycle becomes smaller than a second difference between the first gas feeding time period and the first gas discharging time period.

19. The insufflation device according to claim 18, wherein the processor is configured to increase the gas feeding amount per unit time such that the second gas feeding time period is shorter than the first gas feeding time period.

* * * * *